(12) United States Patent
Pancholy et al.

(10) Patent No.: US 11,103,746 B2
(45) Date of Patent: Aug. 31, 2021

(54) INCENTIVE SPIROMETER CAP

(71) Applicants: Bharat Pancholy, Los Gatos, CA (US); Gregory Brian Gulliver, Grayslake, IL (US)

(72) Inventors: Bharat Pancholy, Los Gatos, CA (US); Gregory Brian Gulliver, Grayslake, IL (US)

( * ) Notice: Subject to any disclaimer, the term of this patent is extended or adjusted under 35 U.S.C. 154(b) by 0 days.

(21) Appl. No.: 16/739,860

(22) Filed: Jan. 10, 2020

(65) Prior Publication Data

US 2020/0179751 A1    Jun. 11, 2020

Related U.S. Application Data

(62) Division of application No. 15/619,465, filed on Jun. 10, 2017, now Pat. No. 10,569,132.

(51) Int. Cl.
| | | |
|---|---|---|
| *A63B 23/18* | (2006.01) | |
| *A61M 16/04* | (2006.01) | |
| *A61M 16/08* | (2006.01) | |
| *A61L 2/10* | (2006.01) | |
| *A61B 5/087* | (2006.01) | |
| *A61L 2/232* | (2006.01) | |
| *A61M 16/00* | (2006.01) | |

(52) U.S. Cl.
CPC ............. *A63B 23/18* (2013.01); *A61B 5/087* (2013.01); *A61L 2/10* (2013.01); *A61L 2/232* (2013.01); *A61M 16/0488* (2013.01); *A61M 16/0875* (2013.01); *A61L 2202/11* (2013.01); *A61L 2202/24* (2013.01); *A61M 2016/003* (2013.01); *A61M 2205/0205* (2013.01); *A61M 2205/053* (2013.01); *A61M 2205/11* (2013.01); *A61M 2205/3334* (2013.01)

(58) Field of Classification Search
CPC . A61B 5/087; A61L 2/10; A61L 2/232; A61L 2202/11; A61L 2202/24; A61M 16/0488; A61M 16/0875; A61M 2016/003; A61M 2205/0205; A61M 2205/053; A61M 2205/11; A61M 2205/3334; A63B 23/18
See application file for complete search history.

(56) References Cited

U.S. PATENT DOCUMENTS

| | | | | |
|---|---|---|---|---|
| 3,695,608 A | * | 10/1972 | Hanson | A63B 23/18 482/13 |
| 4,096,855 A | * | 6/1978 | Fleury, Jr. | A61B 5/0935 482/13 |
| 4,138,105 A | * | 2/1979 | Hunger | A63B 23/18 482/13 |
| 4,171,804 A | * | 10/1979 | Thead, Jr. | A63B 23/18 482/13 |
| 4,363,328 A | * | 12/1982 | Poirier | A61B 5/093 482/13 |
| 4,425,923 A | * | 1/1984 | Gordon | A61B 5/0875 482/13 |
| 4,441,506 A | * | 4/1984 | McCombs | A63B 23/18 482/13 |
| 4,499,905 A | * | 2/1985 | Greenberg | A61B 5/091 482/13 |

(Continued)

*Primary Examiner* — Joshua Lee
(74) *Attorney, Agent, or Firm* — Gregory B. Gulliver

(57) ABSTRACT

An incentive spirometer medical device having a mouth piece protected by an enclosure when not in use and being able to be operated by one hand to open to access the mouth piece.

3 Claims, 7 Drawing Sheets

(56) References Cited

U.S. PATENT DOCUMENTS

| | | | | |
|---|---|---|---|---|
| 5,431,154 | A * | 7/1995 | Seigel | A61M 15/0086 |
| | | | | 128/200.14 |
| 6,126,613 | A * | 10/2000 | Edwards | A61B 5/09 |
| | | | | 600/538 |
| 6,656,129 | B2 * | 12/2003 | Niles | A61B 5/0875 |
| | | | | 600/532 |
| 9,770,566 | B2 * | 9/2017 | Meyers | A61M 16/0051 |
| 10,092,713 | B2 * | 10/2018 | Terry | A61M 11/041 |
| 2007/0042870 | A1 * | 2/2007 | Bohman | A63B 23/18 |
| | | | | 482/11 |
| 2009/0239711 | A1 * | 9/2009 | Foley | A63B 71/0619 |
| | | | | 482/13 |
| 2009/0242587 | A1 * | 10/2009 | Bemis | A45F 3/20 |
| | | | | 222/92 |
| 2012/0279503 | A1 * | 11/2012 | Zhou | A41D 13/1192 |
| | | | | 128/205.27 |
| 2013/0200104 | A1 * | 8/2013 | Whitehead | F24H 1/142 |
| | | | | 222/146.5 |
| 2013/0204151 | A1 * | 8/2013 | Amirkhanian | A61M 16/10 |
| | | | | 600/538 |
| 2014/0274568 | A1 * | 9/2014 | Lau | A63B 23/18 |
| | | | | 482/13 |
| 2016/0001108 | A1 * | 1/2016 | Zhou | A61L 9/00 |
| | | | | 128/863 |
| 2016/0375213 | A1 * | 12/2016 | Zlupko | A61M 16/0488 |
| | | | | 128/200.24 |
| 2017/0007159 | A1 * | 1/2017 | Dieffenderfer | A61B 5/09 |
| 2017/0265778 | A1 * | 9/2017 | Reichlyn | A61B 5/097 |
| 2018/0312326 | A1 * | 11/2018 | Haden | A61J 9/0661 |

* cited by examiner

US 11,103,746 B2

INCENTIVE SPIROMETER CAP

RELATED APPLICATION

This application claims priority to and is a Divisional Application of U.S. patent application Ser. No. 15/619,465 filed on Jun. 10, 2017, titled "INCENTIVE SPIROMETER CAP", which is also incorporated by reference.

TECHNICAL FIELD

The present disclosure relates to medical devices and more particularly to an incentive spirometer.

BACKGROUND

At present, it is common for patients in hospitals to be given a spirometer, such as the incentive spirometer after surgery. An incentive spirometer is a medical device used to help patients improve the functioning of their lungs. It is provided to patients who have had surgery that might jeopardize respiratory function, particularly surgery to the lungs themselves, but also commonly to patients recovering from cardiac or other surgery involving extended time under anaesthesia and prolonged in-bed recovery. The incentive spirometer is also issued to patients recovering from pneumonia or rib damage to help minimize the chance of fluid build-up in the lungs. It can be used as well in non-medical applications, such as by wind instrument players, who want to improve their air flow.

The patient breathes in from the device as slowly and as deeply as possible, and then holds their breath for 2-6 seconds. This provides back pressure which pops open the alveoli. It is a similar manoeuvre as yawning. An indicator provides a gauge of how well the patient's lung or lungs are functioning, by indicating sustained inhalation vacuum. The patient is generally asked to do many repetitions a day while measuring his or her progress by way of the gauge.

When the spirometer is not in use it is simply placed on a table, bed, or other surface. A problem exists, because spirometers do not have covers for the mouth piece portion that is inserted into patient's mouths. Also, patient's visitors, nurses, doctors, and other health care providers are also vectors for transmitting viral or bacterial infection onto the mouthpiece. Thus, virus and bacteria may soil the mouth piece by people (including the user) touching the mouth piece portion or by dropping the spirometer on the floor. Further, when patients change rooms, their belongings are often placed in a bag that is put on the bed as the bed is moved. Once again the mouth piece portion may be in contact with undesirable and unclean items and surfaces. Yet another way the mouth piece may become dirty or infected, is people in the room coughing and sneezing. When hospitalized patients obtain a secondary infection, or a super infection, it prolongs their hospital stay, hospital cost, and increase the duration of overall healthcare treatment.

As such, there is a need for an approach to protect the mouth piece of an incentive spirometer when it is not in a patient's mouth. It is with respect to these and other considerations that the disclosure made herein is presented.

SUMMARY

It would be desirable to protect the mouth piece of the incentive spirometer using an enclosure that is able to be operated by impaired or recovering individuals. The enclosure may be opened by a patient using one hand and closed use. The enclosure also needs to be secured to the incentive spirometer in both the open and closed position to prevent the enclosure from be dropped (contaminated) or lost. The enclosure for the incentive spirometer may also be composed of anti-bacteria material or material coated with anti-bacterial property to provide additional protection.

In another embodiment, an opening may be incorporated into the incentive spirometer, such that the mouth piece is inserted into the incentive spirometer housing. The void may be coated anti-bacterial material and/or ultraviolet lighting may be used to reduce or remove bacteria that may exist on the incentive spirometer's mouthpiece.

Therefore, the above approach addresses the unmet need in the marketplace by elimination of unprotected incentive spirometer mouth pieces and in the process decreasing the risk of infection in patients.

BRIEF DESCRIPTION OF THE DRAWINGS

Preferred features of the present invention will now be described, purely by way of example, with reference to the accompanying drawings, in which.

DETAILED DESCRIPTION OF EMBODIMENTS

Figure 1:
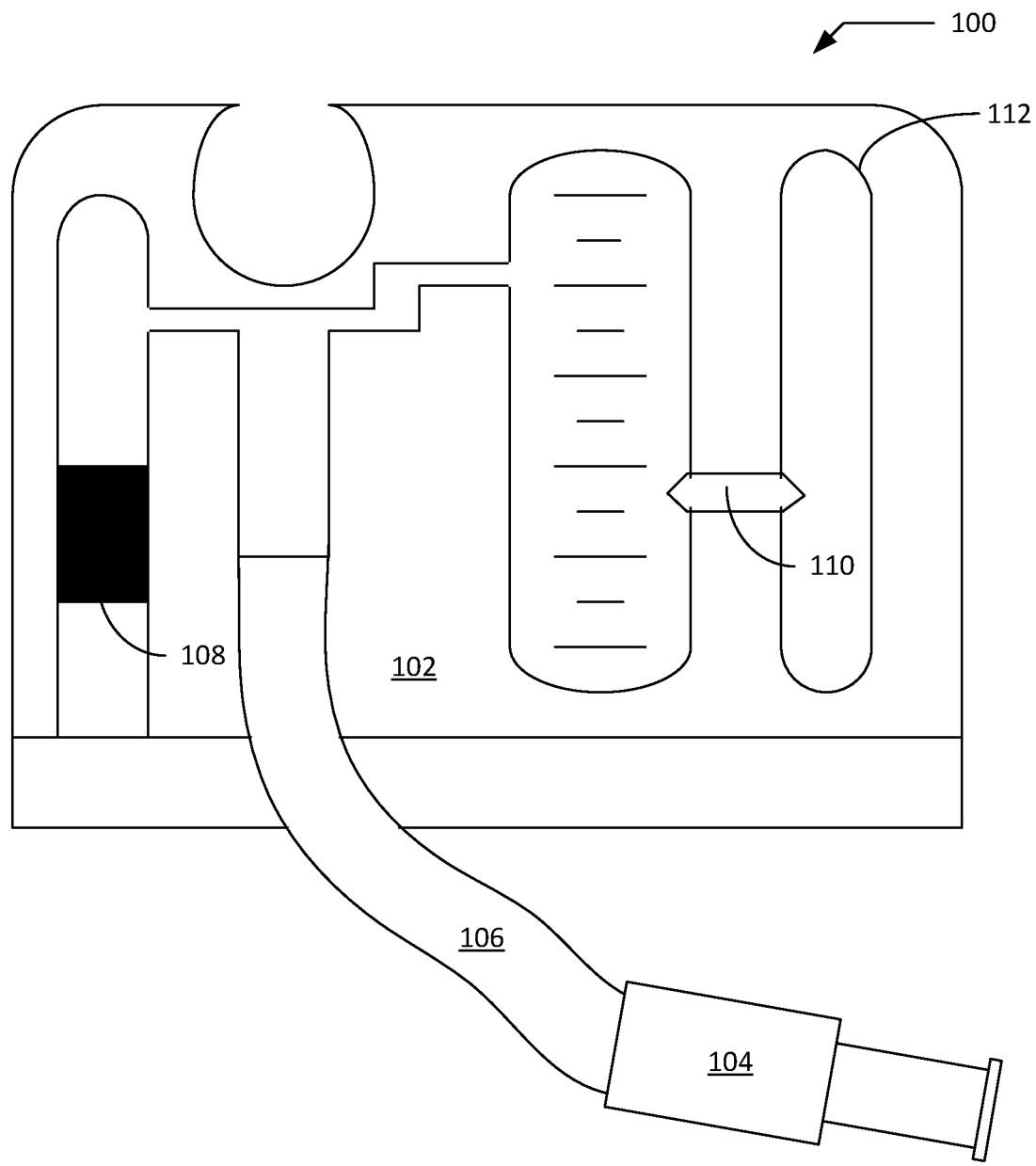
FIG. 1 illustrates a known incentive spirometer.

In FIG. 1, an illustration of a known incentive spirometer 100 is depicted. The spirometer 100 has a housing 102 with a hose 106 connected to the housing and mouth piece 104 at the end of the hose 106. A patient is given incentive spirometer 100 to use in a hospital after an operation an instructed to place the mouth piece 104 in their mouth and inhales slowly and as deeply as possible ten times every hour. A float 108 moves in response to the inhaling action and the sustained inhalation vacuum that may be recorded using marker 110. A hand hold is defined by opening 112 in housing 102.

Figure 2:
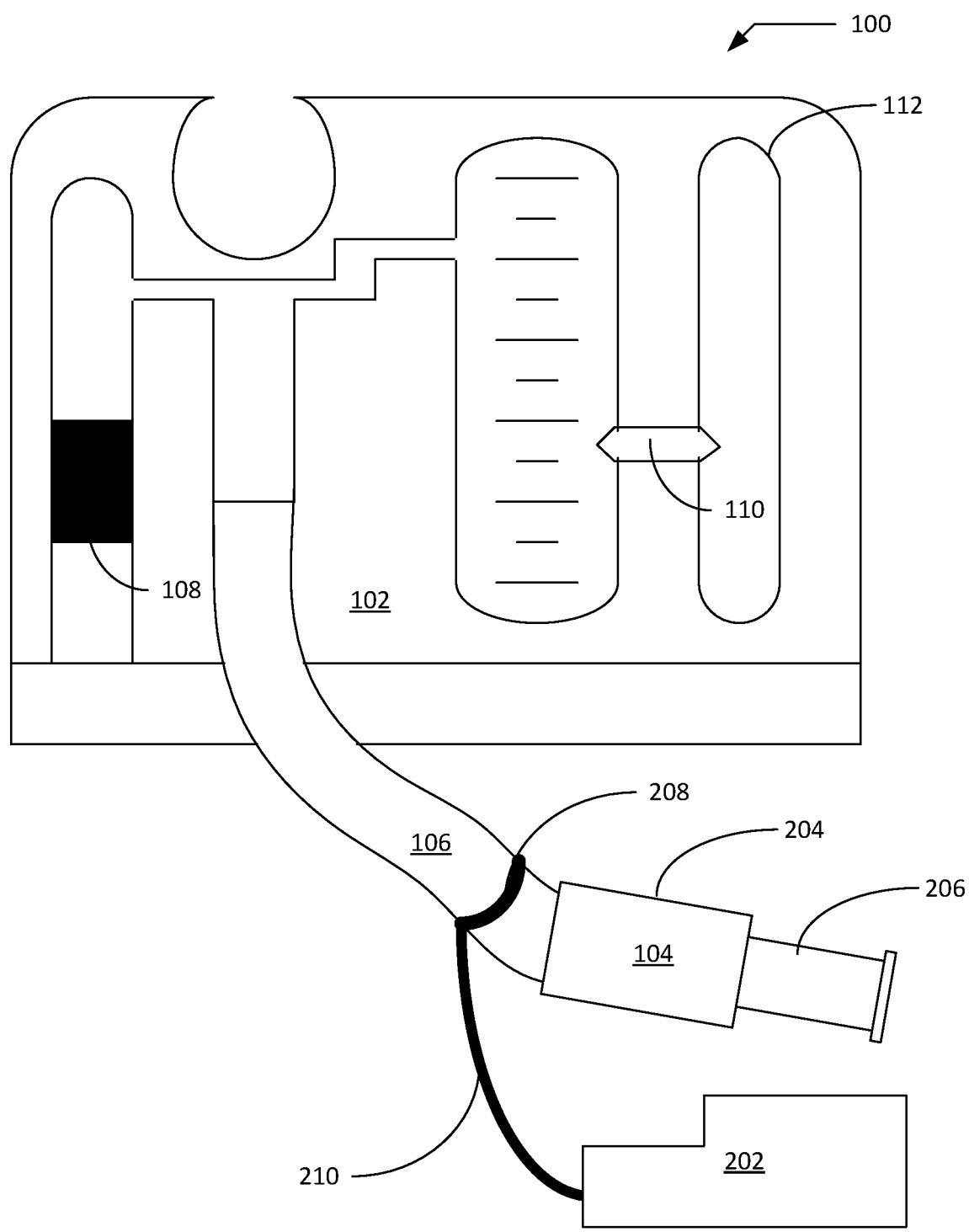
FIG. 2 illustrates the incentive spirometer of FIG. 1 with a protective enclosure in accordance with an example implementation.

Turing to FIG. 2, an illustration of the incentive spirometer of FIG. 1 with a protective enclosure 202 in accordance with an example implementation of the invention is depicted. The enclosure 202 is formed so it clips to the bottom portion 204 of mouth piece without going fully around bottom portion 204, while completely enclosing lip portion 206 of the mouth piece 104. The mouth piece 104 is coupled to a first end of the hose 106 and the second end of the hose 106 is coupled to the housing 102. A patient may use a single hand to pry off the clipped enclosure 202 using their thumb. Similarly a patient may clip on the enclosure 202 to the mouth piece 104 using a single hand. The enclosure 202 is secured to the spirometer 100 via ring 208 and tether 210. The tether 210 and ring 208 may be integrated together in some implementations. In other implementations, the tether 210 may be integrated the hose 106. The housing 102 may be formed out of a plastic material, such as a polymer.

The enclosure 202 may be made out a solid material such of plastic, glass, or other mouldable substances. The mouldable substances may contain anti-bacterial material such as silver or other anti-bacterial additives, such as BIOMASTER. A common name for such substances is anti-bacterial polymers.

Figure 3:
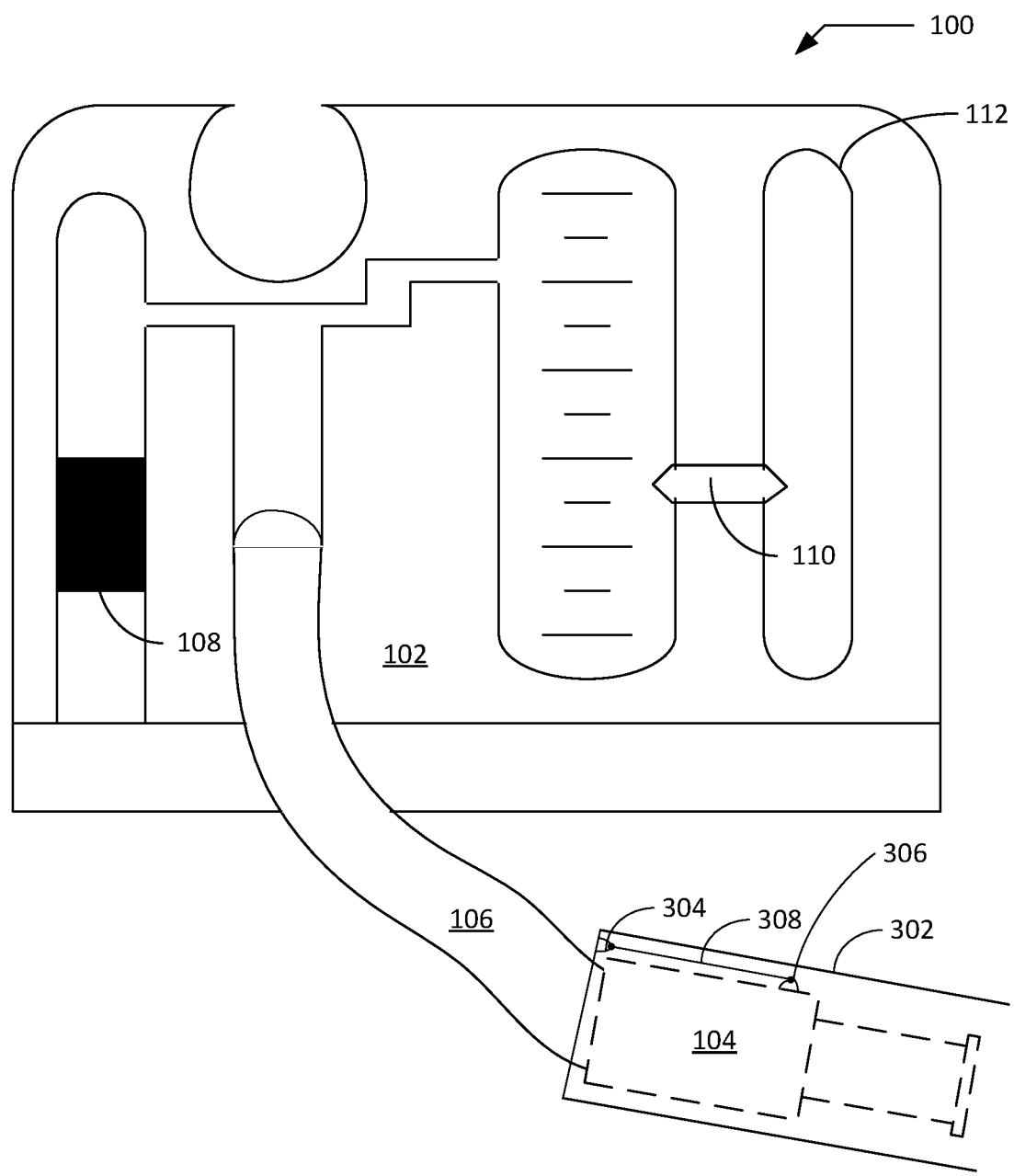
FIG. 3 illustrates the incentive spirometer of FIG. 1 with anther embodiment of an enclosure in accordance with an example implementation.

In FIG. 3, an illustration of the incentive spirometer 100 of FIG. 1 with anther embodiment of an enclosure 302 in accordance with an example implementation of the invention is depicted. The enclosure 302 is biased in a closed position around the mouth piece 104. A connector member 304 and 306 enable a spring or elastic material 308 to be secured to the enclosure 302 and mouth piece 104. When the enclosure 302 is pulled back (towards the hose 106), the mouth piece 104 is exposed for use. The spring or elastic material 308 is stretched exerting a closing or covering force on the enclosure 302. When the enclosure 302 is released, it automatically covers the mouth piece 104 of the spirometer.

As previously explained, anti-bacterial polymers or coatings may be employed on or in the enclosure 302.

Figure 4:
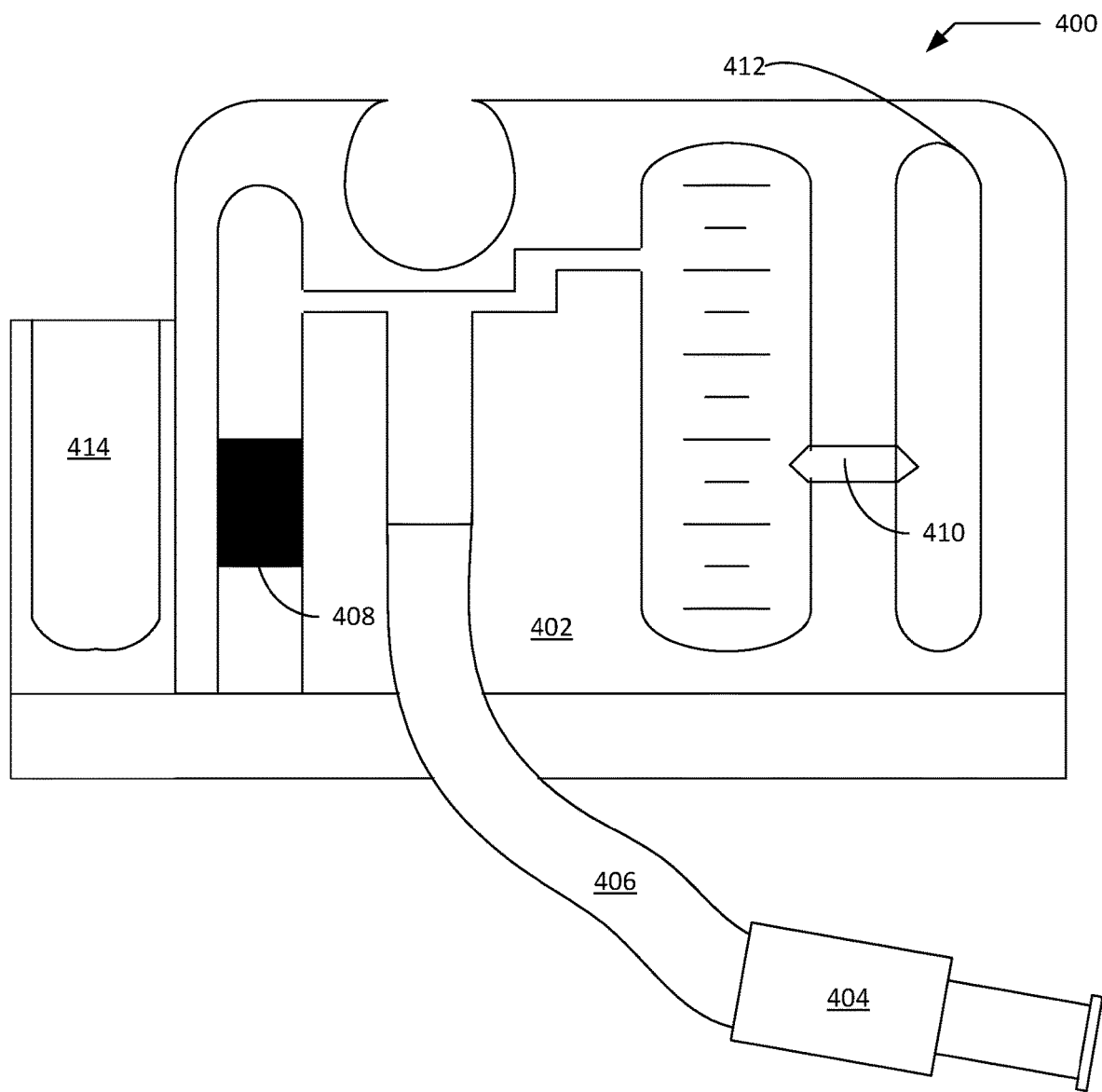
FIG. 4 illustrates an incentive spirometer housing having a recess defined by the housing for storage of the mouth piece of the incentive spirometer in accordance with an example implementation.

Turning to FIG. 4, an illustration of an incentive spirometer housing 402 having a recess 414 defined by the housing 402 for storage of the mouth piece 404 in the spirometer 400 in accordance with an example implementation of the invention is depicted. The housing 402 is formed or moulded with a recess 414 large enough to place the mouthpiece 404 into. The hose 406 may be connected to the mouth piece 404 while it is in recess 214. In other implementations, the mouth piece 404 may be removed from hose 406 and stored in the recess 414. In other implementations, at least the portion of the housing 402 forming recess 414 is made out of an anti-bacterial polymer.

A patient is given incentive spirometer 400 to use in a hospital after an operation an instructed to inhale from the mouth piece 404 ten times every hour. A float 408 moves in response to the inhaling action and may be recorded using marker 110. A hand hold is defined by opening 412 in housing 402.

Figure 5:
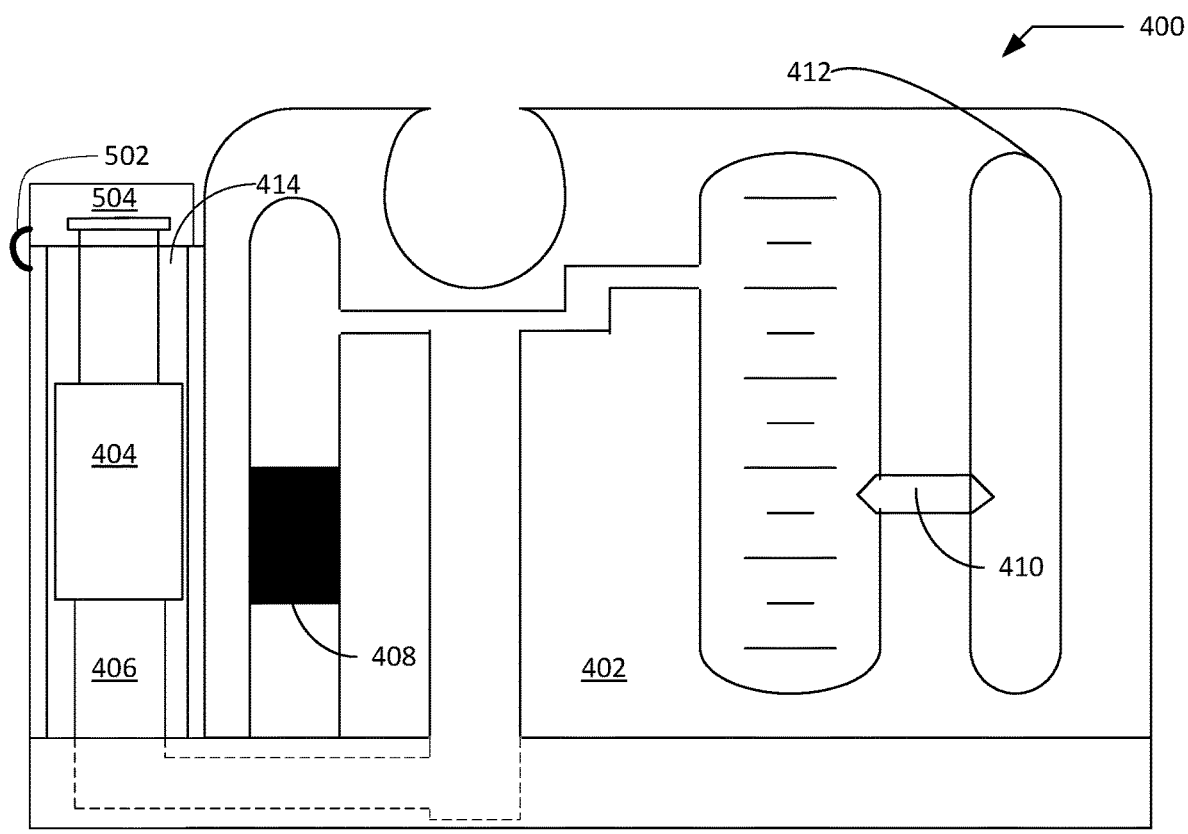
FIG. 5 illustrates an incentive spirometer housing of FIG. 4, where the mouth piece extends from the recess defined by the housing.

In FIG. 5, an illustration of an incentive spirometer housing 402 of FIG. 4, where the mouth piece 404 extends from the recess 414 defined by the housing 402 of spirometer 400 is depicted in accordance with an example implementation of the invention. The mouth piece 404 is coupled to a first end of a coiled or stretchable hose 406 and rests in recess 414. The second end of the hose 406 is coupled to housing 402. The recess 414 is covered by a cap 504 that held in place by friction in the current implementation. In other implementations, other known approaches for securing the cap may be employed, including threads, tabs, etc. . . .

The cap 504 is secured to the housing 402 via a connector 502. The connector 502 may be formed out of the same material as the cap 504, such as a polymer. In other implementations, a ring may be associated with the cap where the cap is secured to a ring by a tab 502 and the ring secured to the housing 402. In yet other implementations, the hose be of a fixed length and further extend into the base of the spirometer 400.

Figure 6:
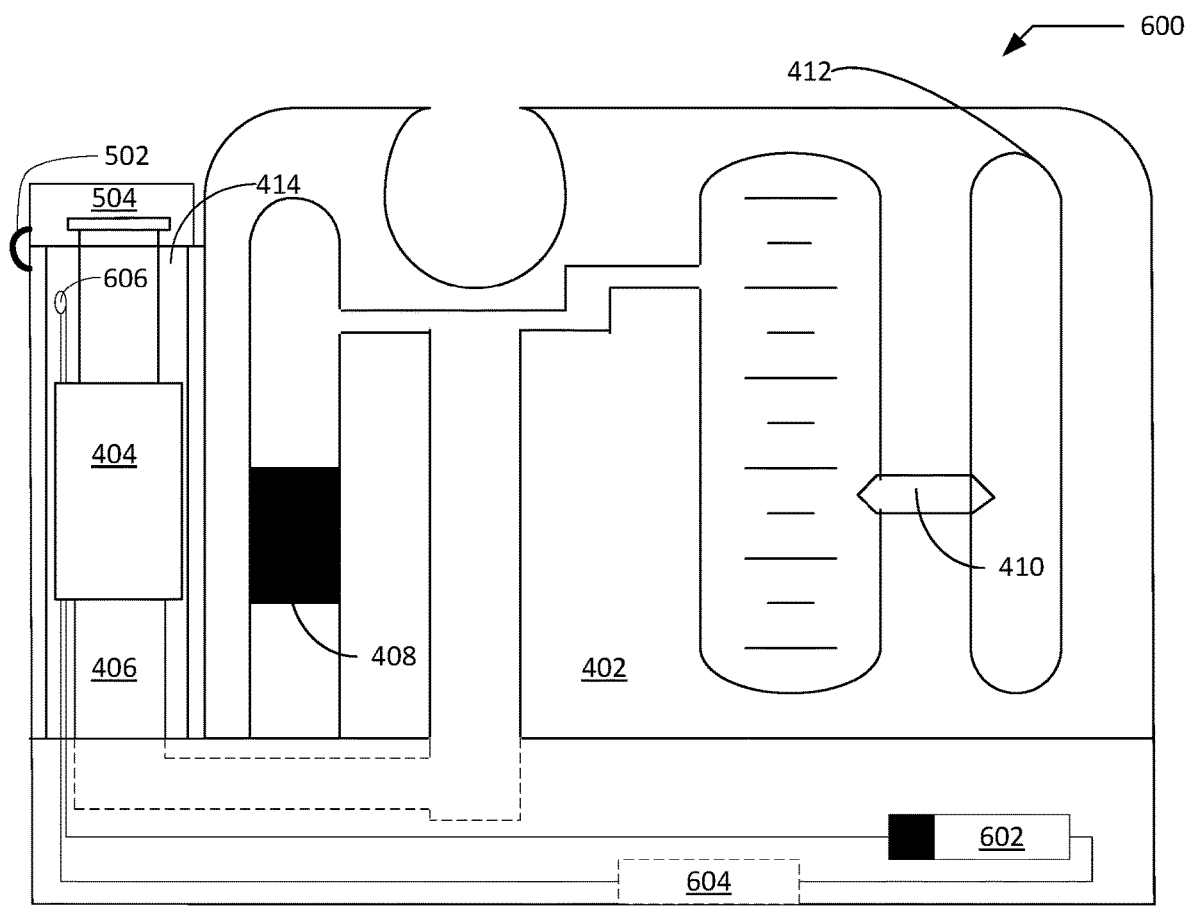
FIG. 6 illustrates an incentive spirometer housing of FIG. 5, where the mouth piece extends from the recess defined by the housing.

Turning to FIG. 6, an illustration of the incentive spirometer housing 402 of FIG. 5, where the mouth piece 404 extends from the recess 414 defined by the housing 402 is depicted in accordance with an example implementation of the invention. A switch 602 is coupled to a power supply 604 and ultra-violet light emitting diodes (ULEDs) 606 (only one is shown in FIG. 6, but in practice more may be in recess 414). The ULEDs 606 illuminate the recess 414 with ultra-violet light when switched on by switch 602 using current from power supply 604. The ultra-violate light from the ULEDs 606 then kills and/or inhibits bacteria and virus growth that may be present on the mouth piece 404. The wave length of the ULEDs may be 365 nm (manufactured by Nichia Corporation, wavelength 365 nm, output 15 mW/cm$^2$) in the current implementation. The power supply 604 may be implemented with batteries, such as alkaline, or NiMH, Lithium-metal, lead acid, gel-cell, or other electric generating approaches. A cap 504 and connector 502 are shown covering the recess 414.

Figure 7:
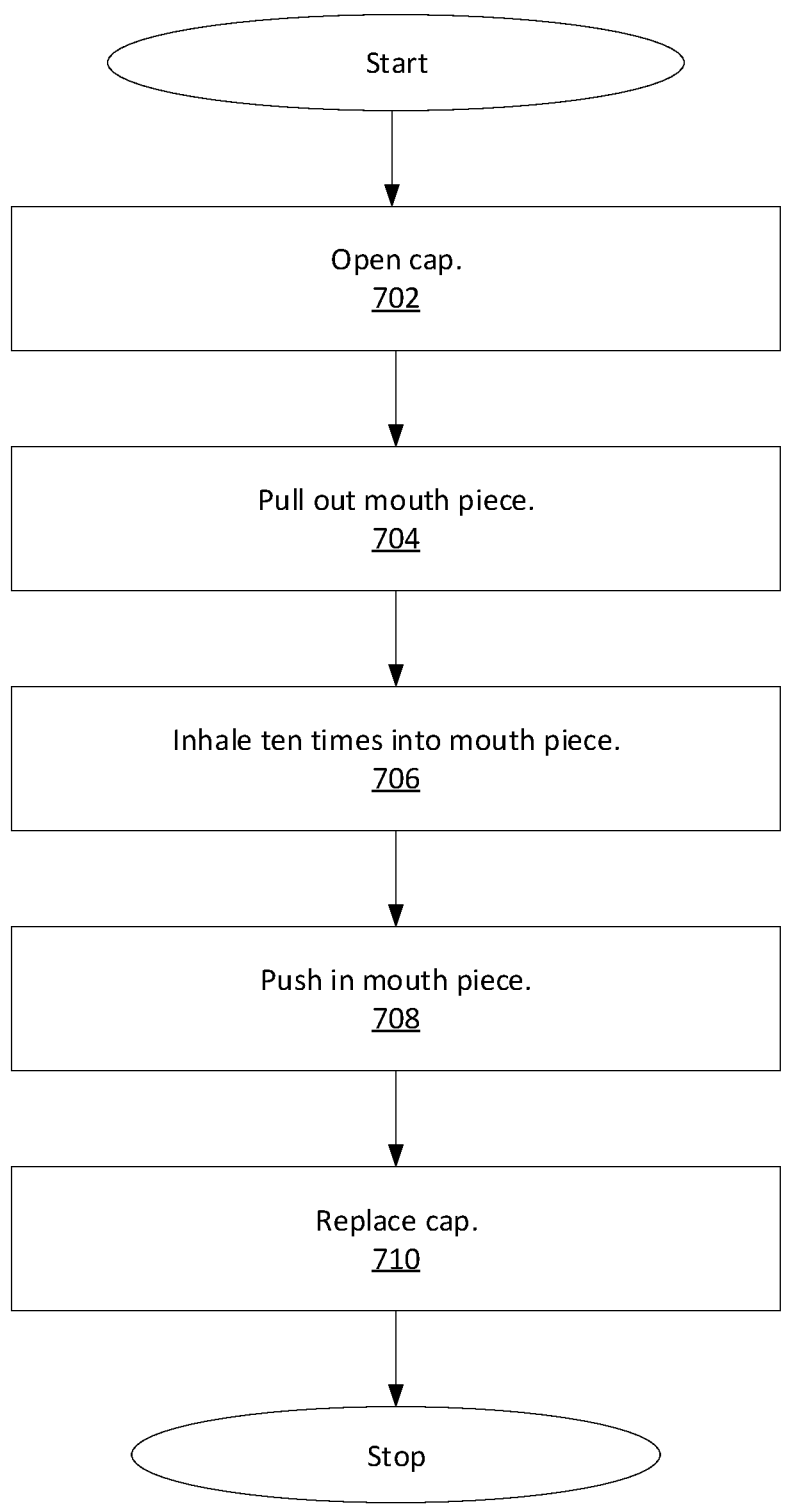
FIG. 7 is a flow diagram of the method of use of the incentive spirometer of FIG. 5 in accordance with an example implementation.

In FIG. 7, a flow diagram of the approach of using the incentive spirometer 400 of FIG. 5 is depicted in accordance with an example implementation. A patient starts using the spirometer 400 by opening the cap 504 in step 702. The patient then pulls out the mouth piece 404 that is coupled to tube 402 from recess 414 in step 704. The patient then inhales ten times from the mouth piece 404 in step 706. The mouth piece 404 and hose 406 are then pushed back into recess 414 in step 708 when finished. The cap 504 is then replaced in step 710.

It will be understood that the present invention has been described above purely by way of example, and modification of detail can be made within the scope of the invention. Each feature disclosed in the description, and (where appropriate) the claims and drawings may be provided independently or in any appropriate combination.

The invention claimed is:

1. A medical device, comprising:
 a hose having a first end and a second end;
 a mouthpiece coupled to a first end of the hose; and
 an incentive spirometer having a housing coupled to the second end of the hose, and where the housing forms a cavity adapted to secure the mouthpiece, wherein an ultraviolet light source illuminates the cavity.

2. The medical device of claim 1, wherein the ultraviolet light source is responsive to a switch located in the housing.

3. The medical device of claim 2, wherein the switch is activated upon the mouthpiece being placed in the cavity.

* * * * *